United States Patent
Srikar et al.

(10) Patent No.: US 11,702,446 B2
(45) Date of Patent: Jul. 18, 2023

(54) ACYLATION PROCESS FOR PREPARATION OF N-SUBSTITUTED PEPTIDE

(71) Applicant: LEVIM BIOTECH LLP, Chennai (IN)

(72) Inventors: Raman Srikar, Chennai (IN); Vimal Jatin, Chennai (IN); Sreedurgalakshmi K, Chennai (IN)

(73) Assignee: LEVIM BIOTECH LLP, Chennai (IN)

( * ) Notice: Subject to any disclaimer, the term of this patent is extended or adjusted under 35 U.S.C. 154(b) by 0 days.

(21) Appl. No.: 17/413,463

(22) PCT Filed: Jun. 29, 2019

(86) PCT No.: PCT/IB2019/055537
§ 371 (c)(1),
(2) Date: Jun. 11, 2021

(87) PCT Pub. No.: WO2020/121071
PCT Pub. Date: Jun. 18, 2020

(65) Prior Publication Data
US 2022/0135615 A1  May 5, 2022

(30) Foreign Application Priority Data
Dec. 12, 2018  (IN) .............................. 201841047057

(51) Int. Cl.
*C07K 1/10* (2006.01)
*C07K 1/107* (2006.01)

(52) U.S. Cl.
CPC .................................. *C07K 1/1077* (2013.01)

(58) Field of Classification Search
CPC .............................. C07K 1/1077; C07K 14/605
See application file for complete search history.

(56) References Cited

U.S. PATENT DOCUMENTS

| 6,451,974 | B1 * | 9/2002 | Hansen | ................ C07K 14/605 |
| | | | | 530/308 |
| 7,273,921 | B2 * | 9/2007 | Dunweber | ......... G01N 33/6842 |
| | | | | 530/308 |
| 2014/0350219 | A1 | 11/2014 | Pan et al. | |

FOREIGN PATENT DOCUMENTS

| CA | 2449296 A1 | 9/1996 |
| WO | 2014199397 A2 | 12/2014 |
| WO | 2016059609 A1 | 4/2016 |
| WO | 2016145388 A1 | 9/2016 |
| WO | 2018116178 A1 | 6/2018 |

OTHER PUBLICATIONS

Commission of the European Communities, N-Methylpyrrolidone, May 2001, Total pp. 7, <URL:http://www3.imperial.ac.Uk/pls/portallive/docs/1/7276131.PDF>.
Tanaka, H et al. Direct determination of naturally occurring biologically active compound serum albumin conjugate by matrix-assisted laser desorption/ionization mass spectrometry, Spectroscopy, vol. 15, 2001, pp. 1-18; Total pp. 18.

* cited by examiner

*Primary Examiner* — Sudhakar Katakam
(74) *Attorney, Agent, or Firm* — Sundar Subramanyam, Esq.

(57) ABSTRACT

The present invention relates to a facile acylation process for preparation of N-Substituted peptide and proteins. More specifically, the invention relates to acylating a peptide or a protein with deprotected acylating agent.

28 Claims, 6 Drawing Sheets

ACYLATION PROCESS FOR PREPARATION OF N-SUBSTITUTED PEPTIDE

FIELD OF THE INVENTION

The present invention relates to a facile acylation process for preparation of N-Substituted peptide and proteins. More specifically, the invention relates to acylating a peptide or a protein with deprotected acylating agent.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Primary amine derivatization is becoming increasingly ubiquitous for applications such as attachment of lipophilic side chains to specific amino acids of peptides and proteins. For the purpose of conjugation or attachment, the widely used moiety comprises of lipophilic side chain modified with esters of N-hydroxysuccinimide (NHS). More specifically, the carboxylic functional group of the lipophilic side chain is converted to amine reactive functional group, vis-à-vis reactive esters, using NHS. The reactive ester is subsequently attached to the main chain of peptide or protein to obtain the N-substituted amide analogue. However, there are instances wherein the functional group in the lipophilic chain comprises of two or more carboxyl groups (for example, presence of amino acids such as glutamic acid, aspartic acid in the lipophilic side chain). In such cases, one of the carboxyl groups is terminally protected using non-reactive moieties such as benzyl ester, tertiary butyl ester or methyl ester and the other carboxyl group is modified to the reactive NHS ester. For example, in the case of the drug liraglutide, the ε-amino group of $Lys^{26}$ present in the main chain (called as liraglutide precursor) is acylated with γ-carboxyl group of N-palmitoyl-1-glutamic acid to obtain liraglutide. However, since glutamic acid comprises of two carboxyl groups, the α carboxyl functional group is generally blocked with a protecting group whereas the γ-carboxyl group of the lipophilic side chain is rendered reactive through NHS ester. To obtain liraglutide, the lipophilic side chain is first linked to the precursor through acylation process mediated via amide bond formation through NHS ester of palmitoyl-1-glutamic acid α alkyl ester and subsequently, the blocking group is deprotected.

Several works on the process for acylating a peptide and subsequent deprotection to obtain N-substituted peptide in solution phase has been reported. For Liraglutide, two most common blocking agents used for the carboxyl group of the lipophilic moiety are (i) o-tertiary butyl ester (OtBu) and (ii) o-methyl ester (oMe).

WO2014199397A2 discloses preparation of liraglutide using solid phase peptide synthesis (SPPS). After acylation using Palmitoyl-Glu-OtBu, deprotection was carried out using a cocktail mixture of 90% TFA/5% TIPS/5% Water in the presence of DCM and subsequent extraction with MTBE to obtain crude liraglutide.

WO2016059609A1 discloses the preparation of N-Substituted peptide through forming a copper complex of the peptide and subsequently hydrolyzing the methyl ester protected carboxyl group of the lipophilic moiety in basic conditions.

US20140350219A1 discloses the preparation of liraglutide by Solid Phase Peptide Synthesis (SPPS). Acylation was carried out using Palmitoyl-Glu-OtBu and subsequently deprotected using 90% TFA/5% thioanisole/3% anisole/2% EDT.

The process of obtaining N-Substituted peptides through acylation described in the above inventions is cumbersome. Current methodology for obtaining N-Substituted peptides involves acylation of the peptide followed by deprotection. For example, solution phase acylation of liraglutide is carried out by subjecting the main chain to acylation using N-palmitoyl-1-glutamic acid containing tertiary butyl ester or methyl esters functionally protecting the carboxyl moiety of glutamic acid. Thereafter, the reaction mixture is subjected to various processing to isolate the acylated peptide. Upon isolation, the acylated peptide is subjected to acidic hydrolysis (for Otbu) or base hydrolysis (for OMe) to obtain the crude liraglutide. Acidic hydrolysis is carried out with a solution comprising high percentage of TFA, generally ranging from 50-95%. Exposure of peptides to highly acidic conditions is known to degrade the peptides. Basic conditions on the other hand can cause possible racemization of the α-amino acid fragments of the peptide.

In addition, deprotection of peptides after acylation usually leads to side product impurities, including but not limited to protected acylated peptides, that eventually leads to low yields. For instance, the overall yield as described in US20140350219-A1 is approximately 15%.

Also, U.S. Pat. No. 6,451,974B1 and U.S. Pat. No. 7,273,921B2 discloses the method of acylating peptides using Novel acylating agents. Essentially, the novel acylation agents comprise of N-hexadecanoyl glutamic acid γ-N-hydroxysuccinimide ester, vis-à-vis, an acylation agent without protecting group. In other words, α carboxyl functional group of the acylating agent remains unprotected before acylation and therefore, there is no requirement for subjecting the peptide to harsh acidic environment for hydrolysis of the protecting group. An added advantage for such acylation process is that the product-related side product impurities can be avoided or minimized. However, the preparation of such acylation agent involves the removal of protecting agent from the acylation agent through catalytic hydrogenation using palladium catalyst and carbon paste. The hydrogenated acylating agent was dried before being subjected to several extraction and purification process to obtain N-hexadecanoyl glutamic acid γ-N-hydroxysuccinimide ester as a dry powder. This deprotected acylation agent was subsequently used for acylation of peptide. However, it is well known that hydrogenation reaction significantly raises safety concerns due to the use of highly flammable reagents. Use of palladium and carbon paste mixture with hydrogen is known to pose extreme fire hazard. In addition, the complexity of the process including hydrogenation, filtration and purification to obtain the deprotected acylating agent renders the process economically ineffective for scale-up activities for acylation of peptide.

Further, the use of the acylating agent with deprotected carboxyl group without isolation or purification, for reaction with peptide or protein has not been reported to our knowledge. The use of the deprotected acylating agent without isolation is desirable since it avoids time-consuming unit operations of isolation, purification & drying, but also poses certain challenges for proceeding with the acylation reaction which requires fine control on the parameters of pH, rate of addition and concentration of the deprotected acylating agent solution etc.

Economic viability and ease of scale-up activities is pivotal for commercialization of therapeutic peptides. The aspects of purification process involving deprotection after acylation generally leads to low overall yields while the aspects of complexity of process such as hydrogenation leads to safety concerns and additional steps of isolation & drying results in increased costs & cycle time.

SUMMARY OF THE INVENTION

This summary is provided to introduce a selection of concepts in a simplified form that are further described below in Detailed Description section. This summary is not intended to identify key features or essential features of the claimed subject matter, nor is it intended to be used as an aid in determining the scope of the claimed subject matter.

The present invention aims to overcome the issues in the existing art and provide a method for acylation to obtain N-Substituted peptide. The present invention relates to deprotection of the acylating agent comprising tertiary butyl ester as one of the functional groups and proceeding for acylation without any requirement of further isolation of the deprotected acylation agent enabling facile synthesis of N-Substituted peptide.

The present disclosure in a general aspect provides a process for acylation of a peptide or a protein with an acylating agent having amino acid with at least one carboxyl protecting group and one reactive ester group, comprising the steps of:
(a) deprotection of said acylating agent in solution;
(b) equilibrating the deprotected acylating agent in solution;
(c) reacting solution of deprotected acylating agent to a peptide or a protein present in aqueous solution at basic pH to obtain desired N-Substituted peptide or protein; and
(d) optionally, quenching N-Substituted peptide or protein by addition of acid or primary amine containing moiety.

In another aspect, the present disclosure provides a process for acylation of a peptide or protein using an acylating agent having amino acid with at least one protected carboxyl group and one reactive ester group and comprising of the steps of:
(a) deprotection of acylating agent comprising removal of at least one carboxyl protecting group such as but not limited to butyl ester; such deprotection carried out under acidic conditions in the presence of acids such as but not limited to Trifluoroacetic acid (TFA), formic acid, phosphoric acid and acetic acid;
(b) equilibrating the deprotected acylating agent using a base such as but not limited to alkali metal hydroxide, Triethylamine (TEA) or combination thereof in the presence or absence of N-Methyl-2-pyrrolidone (NMP);
(c) reacting the equilibrated deprotected acylating agent with a peptide or protein in aqueous solution under basic conditions comprising triethylamine, alkali metal hydroxide or combination thereof and aprotic solvents at appropriate rate of addition and at appropriate mole ratio of acylating agent to peptide to obtain N-Substituted peptide or protein; and
(d) optionally, quenching N-Substituted peptide or protein by addition of acid or primary amine containing moiety.

In one aspect, the present disclosure provides a process for introduction of lipophilic moiety into peptides and protein by solution-phase deprotection of the acylation agent prior to acylation and acylating without isolation or purification of the deprotected acylating agent, thus avoiding the steps of hydrogenation, isolation and drying of the acylation agent as required in existing art.

In another aspect, the present disclosure provides a process for introduction of lipophilic moiety into peptides and protein without subjecting it to highly acidic conditions that is known to degrade or hydrolyze peptide bonds leading to undesired impurities and loss of yield.

In yet another aspect, the present disclosure provides a process for achieving optimum acylation of the proteins and peptides with the un-isolated, deprotected acylating agent by controlling the parameters of concentration of acylating agent, hydrolysis and equilibrating conditions, volumetric rate of addition, pH of reaction, composition of peptide buffer and molar ratios of the peptide:acylating agent.

In still another aspect, the present disclosure provides a process for introduction of lipophilic moiety into peptides and protein by solution-phase deprotection of the acylation agent prior to acylation and acylating without isolation or purification of the deprotected acylating agent wherein the N-Substituted peptide or protein obtained in step (c) or step (d) of the process is optionally purified to obtain pure N-substituted/acylated peptide.

These and other features, aspects, and advantages of the present invention will be better understood with reference to the following description and appended claims. Other aspects of the invention will be set forth in the description which follows, and in part will be apparent from the description, or may be learnt by the practice of the invention.

BRIEF DESCRIPTION OF DRAWINGS THE INVENTION

The following drawings form part of the present specification and are included to further illustrate aspects of the present disclosure. The disclosure may be better understood by reference to the drawings in combination with the detailed description of the specific embodiments presented herein.

DETAILED DESCRIPTION

Figure 1:
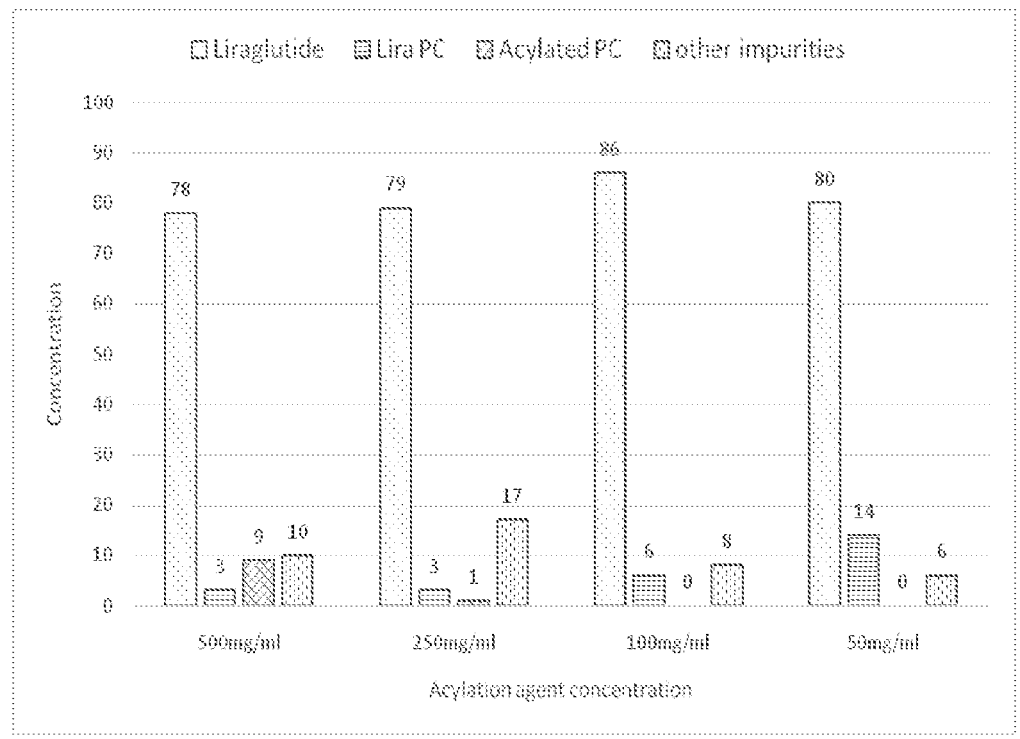
FIG. 1 shows the effect of acylation agent concentration on the acylation process. The figure shows the % composition (by area) of the crude reaction mixture comprising of N-substituted precursor (Liraglutide), unreacted liraglutide precursor (Lira PC), Liraglutide with OtBu protected ester (acylated PC) and reaction related impurities (other impurities).

The following is a detailed description of embodiments of the disclosure. Those skilled in the art will be aware that the present disclosure is subject to variations and modifications other than those specifically described. It is to be understood that the present disclosure includes all such variations and modifications. The detailed disclosure offered is not intended to limit the anticipated variations of embodiments; on the contrary, the intention is to cover all modifications, equivalents, and alternatives falling within the spirit and scope of the present disclosure as defined by the appended claims. The description that follows, and the embodiments described therein, is provided by way of illustration of an example, or examples, of particular embodiments of the principles and aspects of the present disclosure. These examples are provided for the purposes of explanation, and not of limitation, of those principles and of the disclosure.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some embodiments, the numbers expressing quantities of ingredients, properties such as concentration, reaction conditions, and so forth, used to describe and claim certain embodiments of the invention are to be understood as being modified in some instances by the term "about" and/or range values. The recitation of ranges of values herein is merely intended to serve as a shorthand method of referring individually to each separate value falling within the range. Unless otherwise indicated herein, each individual value is incorporated into the specification as if it were individually recited herein. The numerical values presented in some embodiments of the invention may contain certain errors necessarily resulting from the standard deviation found in their respective testing measurements.

The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context requires otherwise, throughout the specification which follow, the word "comprise" and variations thereof, such as, "comprises" and "comprising" are to be construed in an open, inclusive sense that is as "including, but not limited to."

Where a definition or use of a term in an incorporated reference is inconsistent or contrary to the definition of that term provided herein, the definition of that term provided herein applies and the definition of that term in the reference does not apply.

Various terms as used herein are shown below. To the extent a term used in a claim is not defined below, it should be given the broadest definition persons in the pertinent art have given that term as reflected in printed publications and issued patents at the time of filing.

As used herein, the term 'Equilibrate' or 'Equilibrated' or 'Equilibrating' refers to carrying out necessary preparation steps in terms of pH and composition.

As used herein, the term 'PC' or 'Lira PC' or 'Liraglutide precursor' refers to Liraglutide peptide of SEQ ID NO.: 1

As used herein, the term 'OtBu' refers to O-tertiary butyl ester.

As used herein, the term 'Acylated PC' refers to Liraglutide with OtBu protected carboxylic acid.

As used herein, the abbreviation 'DAAS' refers to deprotected acylation agent solution.

As used herein, the abbreviation 'eDAAS' refers to equilibrated deprotected acylation agent solution.

As used herein, the chemical formula 'NaOH' refers to Sodium hydroxide.

As used herein, the unit of measurement 'v/v' refers to volume by volume ratio.

As used herein, the abbreviation 'RP-HPLC' refers to Reverse-Phase High Pressure Liquid Chromatography and 'RT' refers to Room Temperature.

As used herein, the abbreviation 'TEA' refers to Triethylamine; 'TFA' refers to Trifluoroacetic acid; and 'NP' refers to N-Methyl-2-pyrrolidone.

As used herein, the abbreviations 'DEA' refers to Diethylamine; 'DMF' refers to Dimethyl formamide; 'THF' refers to Tetrahydrofuran; 'ACN' refers to Acetonitrile; 'DMSO' refers to Dimethyl sulfoxide; 'TRIS' refers to Tris(hydroxymethyl)aminomethane and 'NHS' refers to N-Hydroxysuccinimide ester.

As used herein, the term 'DsbA' refers to disulfide bond oxidoreductase; 'GST' refers to Glutathione S-transferase; and 'NusA' refers to N-utilization substance.

The present invention involves acylation of peptides and proteins with an acylation agent comprising amino acid with at least one carboxyl protecting group and a reactive ester without subjecting the peptide or protein to the conditions of deprotection adopted ubiquitously for removal of the carboxyl protecting groups. Furthermore, the acylation agent comprising the carboxyl protecting group is deprotected in solution phase and proceeds without any requirement of isolation for the introduction of at least one lipophilic moiety to the peptide or protein.

The present invention provides a process for acylation of a peptide or a protein with an acylating agent having amino acid group with at least one protected carboxyl group and one reactive ester group to obtain a N-substituted peptide or protein. The present invention is useful in the preparation of acylated peptides, including but not limited to therapeutic peptides such as liraglutide.

In an embodiment of the present invention, the peptides or proteins of interest include but are not limited to glucagon-like peptide-1 (GLP-1) and analogues thereof, glucagon-like peptide-2 (GLP-2) and analogues thereof, exendin and analogues thereof, insulin-like growth factor-1 and analogue thereof, insulin-like growth factor-2 and analogues thereof, insulin and analogues thereof, thyroid stimulating hormones, parathyroid hormones, thrombopoietin, hypothalamic releasing factors, adenylate cyclase activating peptide and corticotropin associated factors. In a preferred embodiment of the invention, the peptide is selected from a group comprising GLP-1 analogues, GLP-2 analogues, insulin and analogues thereof. In another preferred embodiment, the GLP-1 analogue is a liraglutide precursor having amino acid sequence as set forth in SEQ ID NO.1: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-Gly.

The present invention provides a process for acylation of a peptide or a protein with an acylating agent, having amino acid with at least one carboxyl protecting group and one reactive ester group, comprising the steps of:
(a) deprotection of said acylating agent in a solution;
(b) equilibrating the deprotected acylating agent in a solution;
(c) reacting the solution of deprotected acylating agent with a peptide or a protein present in an aqueous solution at basic pH to obtain desired N-Substituted peptide or protein; and
(d) optionally, quenching the N-Substituted peptide or protein by addition of acid or primary amine containing moiety.

In another embodiment of the present invention, there is provided a process for acylation of a peptide or protein using an acylating agent having amino acid with at least one protected carboxyl group and one reactive ester group and comprising of the steps of:
(a) deprotection of acylating agent comprising removal of at least one carboxyl protecting group such as, but not limited to, butyl ester;
such deprotection carried out under acidic conditions in the presence of acids such as, but not limited to, trifluoroacetic acid (TFA), formic acid, phosphoric acid and acetic acid;
(b) equilibrating the deprotected acylating agent using a base such as, but not limited to, alkali metal hydroxide, Triethylamine (TEA) or combination thereof in the presence or absence of N-Methyl-2-pyrrolidone (NMP);
(c) reacting the equilibrated deprotected acylating agent with a peptide or protein in aqueous solution under basic conditions comprising triethylamine, alkali metal hydroxide or combination thereof and aprotic solvents at appropriate rate of addition and at appropriate mole ratio of acylating agent to peptide; and
(d) optionally, quenching N-Substituted peptide or protein by addition of acid or primary amine containing moiety.

In an embodiment of the present invention, the acylating agent comprises a lipophilic moiety and amino acid group having at least one protected carboxyl group that can be deprotected by hydrolysis under acidic conditions. The lipophilic moiety of the acylating agent comprises of, but is not limited to, hexadecanoyl acid, hexadecanoyl glutamic acid or analogues thereof. The carboxyl protecting group of the acylating agent is preferably, but not limited to, alkyl ester. Preferably the alkyl ester is butyl ester and more preferably, is tert-butyl ester (otBu). The acylating agent comprises an amine reactive ester such as, but not limited to, imide ester. In a preferred embodiment, the amine reactive ester is N-hydroxysuccinimide ester.

In an embodiment of the present invention, the acylating agent is dissolved in a deprotection solution comprising acid. The deprotection solution is prepared by mixing acid with one or more solvent components selected from a group comprising water, phenol, triisopropylsilane, dioxane, acetone, acetonitrile, N-methyl-2-pyrrolidone (NMP) and dichloromethane. The acid component is selected from a group comprising, but not limited to, TFA, phosphoric acid, formic acid, sulfuric acid and hydrochloric acid. In a preferred embodiment, the deprotection solution comprises 95% TFA and 5% Water.

The use of the acid/water system as in the present invention is advantageous as it negates the use of high volumes of organic solvents such as dimethylformamide, methylene chloride, tetrahydrofuran and the like generally adopted for deprotection in solid phase and solution phase peptide synthesis. The deprotection of the protecting group carried out in the solution of acid and solvent is selective for acid labile functional groups such as tertiary butyl esters.

It is important to control the rate of addition of eDAAS to peptide solution for the reaction to proceed smoothly. Since increasing volumes of eDAAS in peptide solution is directly proportional to the rate of decrease in the pH of the reaction mixture, instantaneous addition of eDAAS to peptide solution lowers the pH of the reaction mixture drastically leading to decreased conversion of liraglutide precursor to liraglutide.

In another embodiment of the present invention, the deprotection of acylating agent is characterized by its concentration in deprotection solution in the range of about 0.1 mg/ml to 1000 mg/ml. Preferably, the concentration of the acylation agent is less than 500 mg/ml, more preferably, the concentration is less than 250 mg/ml and most preferably, the concentration is less than 100 mg/ml. In yet another embodiment, it is preferable to maintain the concentration of the acylating agent in the deprotection solution at 100 mg/ml. The deprotection is carried out at a temperature below 40° C. and preferably carried out at room temperature (RT) of 20° C. to 25° C.

In yet another embodiment, the concentration of the acylating agent at 100 mg/ml facilitates complete deprotection within 1 hour. In addition, the amount of TFA in the deprotected acylation agent is critical for the successive steps of equilibration and acylation. Advantageously, the volume of TFA added to the solution containing peptide or protein should be relatively low since acylation process takes place in basic conditions. Addition of deprotected acylation agent solution also called as 'DAAS' to the solution containing the peptide, referred to as 'peptide solution' herein, triggers reduction in pH instantaneously and if used in excess, might cause negligible acylation.

In another embodiment of the present invention, equilibration of deprotected acylation agent solution is provided for proceeding to acylation without any further processing or purification of the DAAS. Equilibration of DAAS is carried out using an equilibration cocktail comprising aprotic solvent and base solution.

In an embodiment of the present invention, the aprotic solvents is selected from a group comprising, but not limited to, dimethylsulfoxide (DMSO), N-Methyl-2-Pyrrolidone (NMP), dimethylformamide (DMF), tetrahydrofuran (THF), acetonitrile (ACN), acetone, dioxane and combinations thereof. In an embodiment of the present invention, the base solution is selected from, but not limited to TEA, alkali metal hydroxide such as NaOH, and combination thereof.

In another embodiment, the equilibration of the deprotected acylating agent is carried out using various volumetric ratios of alkali metal hydroxide, Triethylamine and NMP. Preferably, the equilibration cocktail comprises TEA, NMP and NaOH at appropriate volumetric ratios. More preferably, the equilibration cocktail has at least 0.1 volume of NMP with respect to 1 volume of DAAS. Preferably, the equilibration cocktail is added to DAAS at a temperature below 25° C., preferably at 0-10° C. and more preferably at 0-4° C.

In yet another embodiment of the present invention, upon addition of the equilibration cocktail to DAAS, the pH of the equilibrated DAAS, referred as eDAAS from hereon, is adjusted in the range of 7 to 12.5 for the reaction to proceed efficiently. Preferably, the pH is in the range of 7-11, more preferably in the range of 8-10, and most preferably in the pH range of 9-10.

In yet another embodiment, the equilibrated solution is used without any purification for the next step of acylation.

In an embodiment of the present invention, the crude acylated peptide/protein is obtained by addition of the eDAAS to a solution containing the peptide or protein of interest, hereon referred to as 'peptide solution'.

In one embodiment of this invention, the peptide or protein of interest is initially dissolved in a suitable aqueous solution comprising a mixture of water, base, acid, aprotic solvent and combinations thereof. The base component includes, but is not limited to, TEA, alkali metal hydroxide and a combination thereof. The acid component is used in the peptide solution for pH adjustments and stabilization and includes, but is not limited to, TFA, phosphoric acid, formic acid, sulfuric acid, hydrochloric acid and a combination thereof. The aprotic solvent is used in the peptide solution for efficient conversion of peptide precursor to acylated peptide and includes, but is not limited to, dimethylsulfoxide (DMSO), N-Methyl-2-Pyrrolidone (NMP), dimethylformamide (DMF), tetrahydrofuran (THF), acetonitrile (ACN), acetone, dioxane and combination thereof.

In yet another embodiment, before the addition of eDAAS to the peptide solution, the pH value of the peptide solution is maintained in the range between 9.0 to 12.5, preferably in the range of 11.0 to 12.0 and more preferably in the range of 11.2 and 11.8. In a further preferred embodiment, the alkali metal hydroxide such as NaOH and acids such as TFA is added to the peptide solution to adjust the pH.

In a preferred embodiment, the peptide is dissolved in a solution containing TEA. Preferably, the volumetric percent of TEA in the solution is maintained below 15%, more preferably between 1-10% and most preferably between 5%-7.5%. In yet another preferred embodiment of the invention, the peptide solution contains acetonitrile as an aprotic solvent. Preferably, the volumetric percent of acetonitrile in the peptide solution is below 50%, more preferably in the range of 0%-40% and most preferably in the range of 0%-30%. In a preferred embodiment, the aprotic solvent, acetonitrile, is present in the range of 5%-15% in the aqueous solution. In yet another embodiment, concentration of the peptide in the peptide solution is less than 50 mg/ml, such as 1 mg/ml to 20 mg/ml, preferably between 1mg/ml and 10 mg/ml and more preferably at 5 mg/ml.

In an embodiment of the present invention, introduction of the lipophilic moiety, vis-à-vis acylating agent to peptide is carried out by controlled addition of eDAAS containing deprotected N-Palmitoyl-L-glutamic-acid-$\alpha$-t-butyl-$\gamma$-succinimidyl ester to the peptide solution containing liraglutide precursor at room temperature. The mole ratio of acylating agent to the liraglutide precursor ranges from 0.1:1 to 10:1, preferably from 0.75:1 to 6:1 and more preferably in the range of 1.5:1 to 3:1. Preferably, an increased mole ratio of acylating agent peptide provides effective and optimum conversion of liraglutide precursor to liraglutide.

In another embodiment of the present invention, the concentration of the liraglutide precursor in the peptide solution is less than 50 mg/ml. Preferably, the concentration of liraglutide precursor is less than 20 mg/ml and more preferably the concentration is less than 10 mg/ml. In a preferred embodiment, the concentration of liraglutide precursor in the peptide solution is 5 mg/ml.

Addition of eDAAS causes drop in the pH thereby affecting the reaction efficacy. Therefore, in one embodiment of the invention, upon addition of eDAAS to the peptide solution containing liraglutide precursor, the pH value of the reaction mixture is adjusted to a range of 10 to 12, preferably to a range of 10.5 to 11.8 and more preferably to a pH range of 11 to 11.5 for efficient acylation. In yet another embodiment of the invention, simultaneous addition of alkali metal hydroxide such as NaOH and eDAAS to the peptide solution containing liraglutide precursor is carried out. In a preferred embodiment, eDAAS and 5N NaOH is added in a controlled fashion such that the pH during the course of addition is maintained in the range of 11.4 to 11.8, thereby leading to efficient acylation.

In yet another embodiment of the present invention, the rate of addition of eDAAS to the peptide solution is controlled such that the rate of addition is less than 50 ml/minute, preferably less than 25 ml/min, more preferably less than 10 ml/min and most preferably less than 5 ml/min.

In an embodiment of the present invention, upon obtaining the crude acylated peptide, vis-à-vis crude liraglutide after the addition of eDAAS, the reaction is quenched by the adjusting the pH of the reaction mixture to about pH 8 by the addition of acid or a primary amine containing compound. Preferably, the reaction is quenched for end sample analyses or terminating the reaction. In a preferred embodiment, the acid for quenching is acetic acid. In another preferred embodiment, the primary amine containing compound for quenching is Tris(hydroxymethyl)aminomethane (TRIS). Preferably, TRIS at pH 8.0 is added to the pH adjusted crude liraglutide reaction mixture to achieve a final concentration of TRIS at about 10 mM to 250 mM, more preferably 25 mM to 100 mM and most preferably at 50 mM.

In an embodiment of the present invention, the N-Substituted peptide or protein is subjected to purification to obtain pure N-substituted/acylated peptide. The crude peptide is subsequently purified according to standard preparative high performance liquid chromatography (HPLC) methods known to those skilled in the art. After purification using HPLC, elutions containing liraglutide with a purity level above 80%, preferably above 90%, more preferably above 95% and even more preferably above 97% is collected. Solvents such as, but not limited to, acetonitrile, methanol, and isopropanol, present in the elutions are removed using conventional techniques such as, but not limited to, rotary evaporators, tangential flow filtration or a combination thereof.

In a further preferred embodiment of the present invention, a process for preparation of N-Substituted liraglutide peptide is provided by the introduction of lipophilic moiety linked to the amine residue of the peptide, such as the lysine residue at 26th position of the liraglutide precursor, comprising the following steps:
   (a) subjecting an acylating agent such as N-Palmitoyl-L-glutamic-acid alpha-t-butyl-gamma-succinimidyl ester to acid hydrolysis;
   (b) equilibration of the deprotected acylating agent in solution;
   (c) re-suspending the liraglutide peptide in an aqueous solution adjusted to basic pH with triethylamine (TEA), diethylamine (DEA), alkali metal hydroxide such as but not limited to sodium hydroxide (NaOH) or a combination thereof;
   (d) addition of the solution obtained from step (b) to the peptide solution present in step (c) at suitable conditions to obtain N-substituted/acylated liraglutide peptide;
   (e) optionally, quenching the solution obtained from step (d) by addition of acid; and
   (f) optionally, subjecting the solution obtained in step (d) or step (e) to purification to obtain pure N-substituted/acylated peptide.

It is important to state that the above embodiments are iterative in nature and a careful selection of parameters for deprotection, equilibration and acylation is required for the preparation of N-Substituted peptide through this novel acylation process. For instance, change in the concentration of peptide in the peptide solution affects the volume of eDAAS required for acylation. This directly leads to change of the pH in the reaction mixture leading to alteration in the conversion efficacy. Indeed, the invention deals with process parameters for efficient acylation to obtain N-Substituted peptide or protein.

While the foregoing describes various embodiments of the disclosure, other and further embodiments of the disclosure may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

The disclosure will now be illustrated with following non-limiting working examples, which is intended to illustrate the working of disclosure and not intended to take restrictively to imply any limitations on the scope of the present disclosure. There is also a scope of logical variations or standard deviation of the parameters detailed in the procedure which would be apparent for a person skilled in the art and therefore, the scope of disclosure extends beyond what is cited in the examples. Nonetheless, the examples are intended to encompass the holistic range of the novelty.

All reagents in the following examples were commercially obtained. Liraglutide precursor preparation is well known in the art and may be prepared by synthetic techniques of peptide synthesis or recombinant DNA techniques as a fusion protein with peptide tags such as but not limited to DsbA, GST, NusA or thioredoxin by cloning the corresponding codon-optimized gene into a pET28 vector system transformed into E. coli BL21 (DE3) host cells. The cells are cultured, then harvested, washed and lysed to obtain the fusion protein from the cells. An enzyme cleavage site can be built into the fusion protein gene construct so as to cleave the liraglutide precursor from the fusion protein after isolating from the cell lysate. The liraglutide precursor obtained from the chemical or biological process is typically purified through chromatography steps such as affinity chromatography, ion exchange chromatography and/or Reverse Phase HPLC (RP-HPLC) and organic solvents such as acetonitrile removed. Organic solvents such as acetonitrile, if present, can be removed under reduced pressure or through buffer exchange. Such purified liraglutide precursors have been used in the examples provided below for the acylation reaction. Alternatively, purified liraglutide precursors may be commercially obtained. The room temperature referred to herein indicates a temperature in the range of 20° C. to 25° C.

Example 1. Preparation of N-Substituted Peptide 250 mg of N-hexadecanoylglutamic acid γ-N-hydroxysuccinimide ester α-tertiary butyl ester as an acylation agent was dissolved in 2.5 ml of 95% TFA: 5% water to obtain a concentration of 100 mg/ml. After 1 hour at room temperature (RT) and under constant stirring, the deprotected N-hexadecanoylglutamic acid γ-N-hydroxysuccinimide ester (DAAS) was equilibrated with one volume of NMP and two volumes of TEA to obtain eDAAS (pH 9, 46 mM) at 0-8° C. 1 gm of liraglutide precursor peptide was pre-dissolved in 200 ml aqueous solution containing 7.5% TEA (v/v), 0.2% TFA (v/v) and 10% acetonitrile. The pH of the aqueous solution was approximately 11.8. 10 ml of eDAAS (46 mM) containing deprotected N-hexadecanoylglutamic acid γ-N-hydroxysuccinimide ester was then added to the aqueous peptide solution at an addition rate of 5 ml/min. The mole ratio of the acylation agent to the liraglutide precursor was 1.5:1. After 10 minutes, pH of the reaction mixture was adjusted to 8.0 using 5N acetic acid and the mixture analyzed using reverse phase-high performance liquid chromatography (RP-HPLC). Analytical RP-HPLC analysis showed the conversion from precursor to liraglutide ranged from 90%-95% by area.

Unless stated specifically, acylated peptide with protecting group (tert-butyl ester) was not detected in any of the examples.

Example 2: Effect of Acylation Agent on Preparation of N Substituted Peptide 250 mg of N-hexadecanoylglutamic acid γ-N-hydroxysuccinimide ester α-tertiary butyl ester (acylation agent) was dissolved in a solution comprising TFA and water. 95% TFA at 5 ml, 2.5 ml, 1.25 ml and 0.625 ml: 5% water provided solutions having a concentration of 50 mg/ml, 100 mg/ml, 250 mg/ml and 500 mg/ml, respectively. After 1 hour at room temperature (RT) and under constant stirring, the deprotected N-hexadecanoylglutamic acid γ-N-hydroxysuccinimide ester (DAAS) was equilibrated with one volume of NMP and two volumes of TEA for each of the hydrolysis reaction to obtain eDAAS (pH 9) at 0-8° C.

1 gm of liraglutide precursor was pre-dissolved in 200 ml aqueous solution containing 7.5% TEA (v/v) and 0.2% TFA (v/v) having concentration of 1.5 mM approximately. The pH of the solution was approximately 11.8. The eDAAS having varying concentrations were added to the peptide solution which resulted in approximately 1.5:1 mole ratio of acylation agent to liraglutide precursor. After 10 minutes, pH of the reaction mixture was adjusted to 8.0 using 5N acetic acid and the mixture was analyzed using reverse phase-high performance liquid chromatography (RP-HPLC).

Yield: As shown in FIG. 1, the analytical RP-HPLC analysis showed the conversion from precursor to liraglutide ranged from 78%-86% by area. At high concentrations of acylation agent, the acylated liraglutide precursor impurity was observed, which is the liraglutide conjugated to protected acylation agent, suggesting improper deprotection of acylation agent. The impurities were observed at acylating agent concentrations higher than approximately 250 mg/ml.

Figure 2:
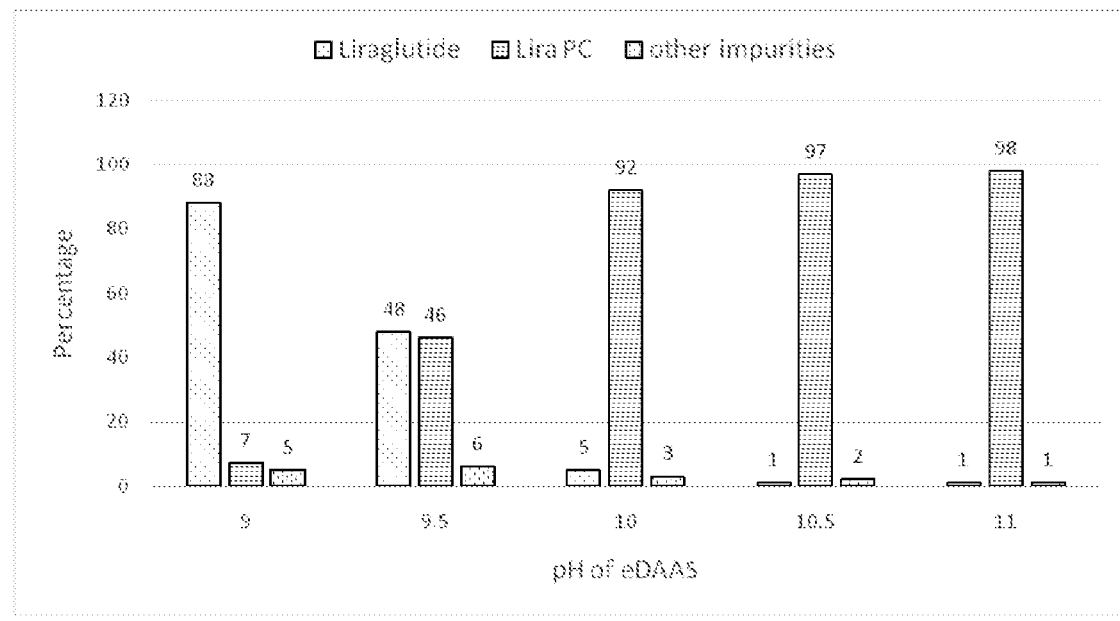
FIG. 2 shows the effect of eDAAS pH on the acylation process. The figure shows the % composition (by area) of the crude reaction mixture comprising of N-substituted precursor (Liraglutide), unreacted liraglutide precursor (Lira PC), and reaction related impurities (other impurities).

Example 3: Effect of pH of Equilibrated Solution on Conversion Efficacy in Preparation of N Substituted Peptide 250 mg of N-hexadecanoylglutamic acid γ-N-hydroxysuccinimide ester α-tertiary butyl ester (acylation agent) was dissolved in 2.5 ml of 95% TFA: 5% water to obtain a concentration of 100 mg/ml. After 1 hour at room temperature and under constant stirring, the deprotected N-hexadecanoylglutamic acid γ-N-hydroxysuccinimide ester (DAAS) was equilibrated with one volume of NMP and two Volumes of TEA to obtain eDAAS (pH 9, 46 mM) at 0-8° C. Subsequently, pH of the eDAAS was adjusted using NaOH to obtain varying pH: 9.0, 9.5, 10.0, 10.5, and 11.0. 1 gm of liraglutide precursor was pre-dissolved in 200 ml aqueous solution containing 7.5% TEA (v/v) and 0.2% TFA (v/v) (approx. concentration 1.5 mM). The pH of the solution was approximately 11.8. Each of the eDAAS comprising varying pH and containing deprotected N-hexadecanoylglutamic acid γ-N-hydroxysuccinimide ester (approx. 46 mM) was then separately added to the peptide solution which resulted in approximately 1.5:1 mole ratio of acylation agent to liraglutide precursor. After 10 minutes, pH of the reaction mixture was adjusted to 8.0 using 5N acetic acid and analyzed using RP-HPLC (FIG. 2).

Yield: As shown in FIG. 2, analytical RP-HPLC analysis showed the conversion to liraglutide sharply ranged from 88% to 1%. Basic pH is clearly less desirable for stability of the N-hydroxysuccinimide ester in eDAAS, but it was found that up to pH 9, high conversion to liraglutide could still be achieved. The results suggest that the reactive ester is highly susceptible to hydrolysis, especially at pH above 9.5. Susceptibility to hydrolysis appears to reduce at pH below 9.5.

Example 4: Effect of pH of Peptide Solution on Conversion Efficacy in Preparation of N Substituted Peptide 250 mg of N-hexadecanoylglutamic acid γ-N-hydroxysuccinimide esterα-tertiary butyl ester (acylation agent) was dissolved in 2.5 ml of 95% TFA: 5% water to obtain a concentration of 100 mg/ml. After 1 hour at room temperature and under constant stirring, the deprotected N-hexadecanoyl glutamic acid γ-N-hydroxysuccinimide ester (DAAS) was equilibrated with one volume of NMP and two volumes of TEA to obtain eDAAS (pH 9, 46 mM) at 0-8° C.

Figure 3:
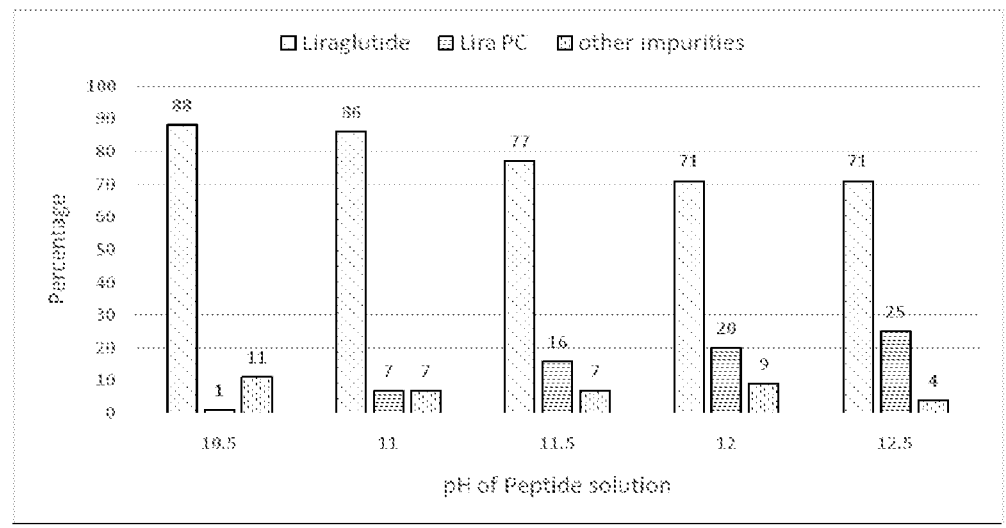
FIG. 3 shows the effect of peptide solution pH on the acylation process. The figure shows the % composition (by area) of the crude reaction mixture comprising of N-substituted precursor (Liraglutide), unreacted liraglutide precursor (Lira PC), and reaction related impurities (other impurities).

1 gm of liraglutide precursor was pre-dissolved in 200 ml aqueous solution containing 7.5% TEA (v/v) and 0.2% TFA (v/v) (approx. concentration 1.5 mM). The pH of the solution was approximately 11.8. Subsequently, pH of the peptide solution was adjusted using HCl and NaOH to varying pH, namely, 10.5, 11.0, 11.5, 12.0, and 12.5. eDAAS (46 mM, 10 ml) containing deprotected N-hexadecanoylglutamic acid γ-N-hydroxysuccinimide ester was then added to each of the peptide solution with varying pH which resulted in approximately 1.5:1 mole ratio of acylation agent to liraglutide precursor. After 10 minutes, pH of the reaction mixture was adjusted to 8.0 using 5 N acetic acid and analyzed using RP-HPLC (FIG. 3).

Yield: As shown in FIG. 3, analytical RP-HPLC analysis showed the conversion to liraglutide ranged from 88% to 71%. A narrow pH range of 10.5-11.5 for the peptide solution within the basic conditions in the acylation reaction was found to support higher conversion to liraglutide.

Example 5: Effect of Aprotic Solvent Concentration in Peptide Solution on Conversion Efficacy in Preparation of N Substituted Peptide 250 mg of N-hexadecanoylglutamic acid γ-N-hydroxysuccinimide ester α-tertiary butyl ester (acylation agent) was dissolved in 2.5 ml of 95% TFA: 5% water to obtain a concentration of 100 mg/ml. After 1 hour at room temperature and under constant stirring, the deprotected N-hexadecanoylglutamic acid γ-N-hydroxysuccinimide ester (DAAS) was equilibrated with one volume of NMP and two volumes of TEA to obtain eDAAS (pH 9, 46 mM) at 0-8° C.

Figure 4:
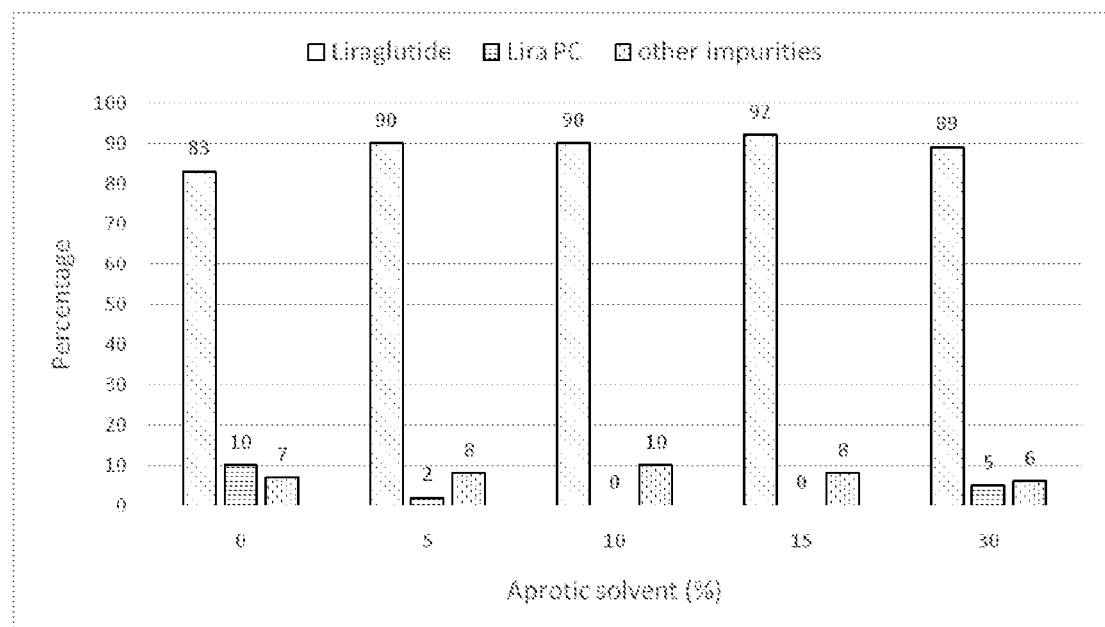
FIG. 4 shows the effect of aprotic solvent % (v/v) in peptide solution on the acylation process. The figure shows the % composition (by area) of the crude reaction mixture comprising of N-substituted precursor (Liraglutide), unreacted liraglutide precursor (Lira PC), and reaction related impurities (other impurities).

1 gm of liraglutide precursor was pre-dissolved in 200 ml aqueous solution containing 7.5% TEA (v/v), 0.2% TFA (v/v) and varying volumetric percent of acetonitrile, namely, 0% v/v, 5% v/v, 10% v/v, 15% v/v and 30% v/v. Concentration of liraglutide peptide was 1.5 mM. The pH of the solution was approximately 11.8. eDAAS (46 mM, 10 ml) containing deprotected N-hexadecanoylglutamic acid γ-N-hydroxysuccinimide ester was then added to each of the peptide solution which resulted in approximately 1.5:1 mole ratio of acylation agent to liraglutide precursor. After 10 minutes, pH of the reaction mixture was adjusted to 8.0 using 5 N acetic acid and analyzed using RP-HPLC (FIG. 4).

Yield: As shown in FIG. 4, analytical RP-HPLC analysis showed the conversion to liraglutide ranged from 83% to 92%. The presence of aprotic solvent in the range of 5%-15% in the aqueous solution was surprisingly found to result in higher conversion of liraglutide precursor to liraglutide.

Example 6: Effect of NMP in Equilibration Cocktail Solution on Conversion Efficacy in Preparation of N Substituted Peptide 250 mg of N-hexadecanoylglutamic acid γ-N-hydroxysuccinimide ester α-tertiary butyl ester (acylation agent) was dissolved in 2.5 ml of 95% TFA: 5% water to obtain a concentration of 100 mg/ml. After 1 hour at room temperature and under constant stirring, 1 volume of deprotected N-hexadecanoyl glutamic acid γ-N-hydroxysuccinimide ester (DAAS) was equilibrated with varying volume of NMP, namely, 0, 0.5, 1.0, 1.5, 2.0 and two volumes of TEA to obtain eDAAS (pH 9, 46 mM) at 0-8° C.

Figure 5:
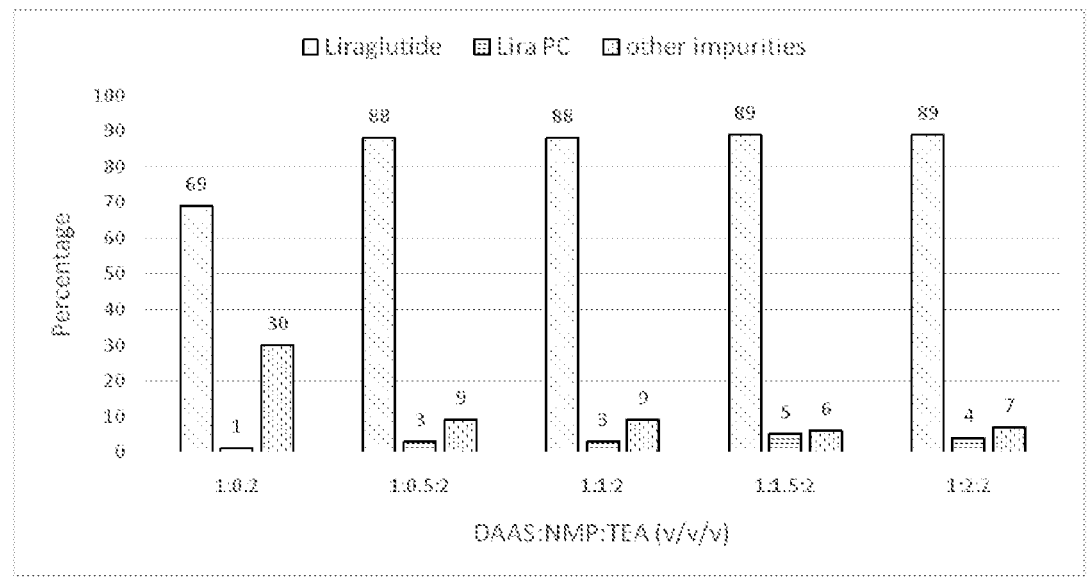
FIG. 5 shows the effect of NMP amount in equilibration cocktail on the acylation process. The figure shows the % composition (by area) of the crude reaction mixture comprising of N-substituted precursor (Liraglutide), unreacted liraglutide precursor (Lira PC), and reaction related impurities (other impurities).

1 gm of liraglutide precursor was pre-dissolved in 200 ml aqueous solution containing 7.5% TEA (v/v) and 0.2% TFA (v/v) (approx. concentration 1.5 mM). The pH of the solution was approximately 11.8. Each of the eDAAS having NMP:DAAS v/v ratio of 0.0, 0.5, 1, 1.5 and 2.0 and containing deprotected N-hexadecanoylglutamic acid γ-N-hydroxysuccinimide ester was then added to the peptide solution which resulted in approximately 1.5:1 mole ratio of acylation agent to liraglutide precursor. After 10 minutes, pH of the reaction mixture was adjusted to 8.0 using 5 N acetic acid and analyzed using RP-HPLC (FIG. 5).

Yield: As shown in FIG. 5, analytical RP-HPLC analysis showed the conversion to liraglutide ranged from 69% to 89%. The presence of NMP at >0.1% in the equilibration solution was surprisingly found to be favorable for the acylation of liraglutide.

Example 7: Effect of TEA in Equilibration Cocktail Solution on Conversion Efficacy in Preparation of N Substituted Peptide 250 mg of N-hexadecanoylglutamic acid γ-N-hydroxysuccinimide ester α-tertiary butyl ester (acylation agent) was dissolved in 2.5 ml of 95% TFA: 5% water to obtain a concentration of 100 mg/ml. After 1 hour at room temperature and under constant stirring, 1 volume of deprotected N-hexadecanoyl glutamic acid γ-N-hydroxysuccinimide ester (DAAS) was equilibrated with one volume of NMP and varying volumes of TEA, namely, 0.0, 1.0, 2.0, 2.5 and 3.0 to obtain eDAAS (pH 9, 46 mM) at 0-8° C.

Figure 6:
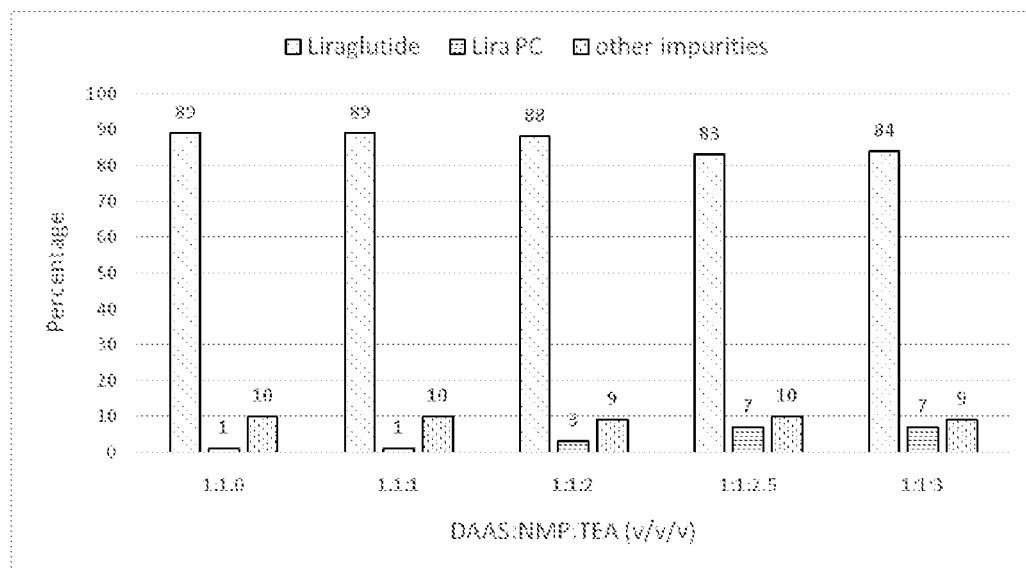
FIG. 6 shows the effect of TEA amount in equilibration cocktail on the acylation process. The figure shows the % composition (by area) of the crude reaction mixture comprising of N-substituted precursor (Liraglutide), unreacted liraglutide precursor (Lira PC), and reaction related impurities (other impurities).

1 gm of liraglutide precursor was pre-dissolved in 200 ml aqueous solution containing 7.5% TEA (v/v) and 0.2% TFA (v/v) (approx. concentration 1.5 mM). The pH of the solution was approximately 11.8. Each of the eDAAS having TEA:DAAS v/v ratio of 0:1. 1:1, 2:1, 2.5:1 and 3:1 and containing deprotected N-hexadecanoylglutamic acid γ-N-hydroxysuccinimide ester was then added to the peptide solution which resulted in approximately 1.5:1 mole ratio of acylation agent to liraglutide precursor. After 10 minutes, pH of the reaction mixture was adjusted to 8.0 using 5 N acetic acid and analyzed using RP-HPLC (FIG. 6).

Yield: As shown in FIG. 6, analytical RP-HPLC analysis showed the conversion to liraglutide ranged from 83% (by area) to 89%. TEA levels below 50% in the equilibration solution were found to favour acylation of liraglutide precursor.

Example 8: Effect of Acylating Agent Mole Ratio on Conversion Efficacy at 7.5% TEA in Preparation of N Substituted Peptide 12.5 mg, 25 mg, 50 mg and 100 mg of N-hexadecanoylglutamic acid γ-N-hydroxysuccinimide esterα-tertiary butyl ester (acylation agent) was dissolved in 0.125 ml, 0.250 ml, 0.5 ml and 1 ml of 95% TFA: 5% water, respectively, to obtain a constant concentration of 100 mg/ml. After 1 hour at room temperature and under constant stirring, 1 volume of deprotected N-hexadecanoyl glutamic acid γ-N-hydroxysuccinimide ester (DAAS) was equilibrated with one volume of NMP and 2 volumes of TEA to obtain eDAAS (pH 9, 46 mM) at 0-8° C.

Figure 7:
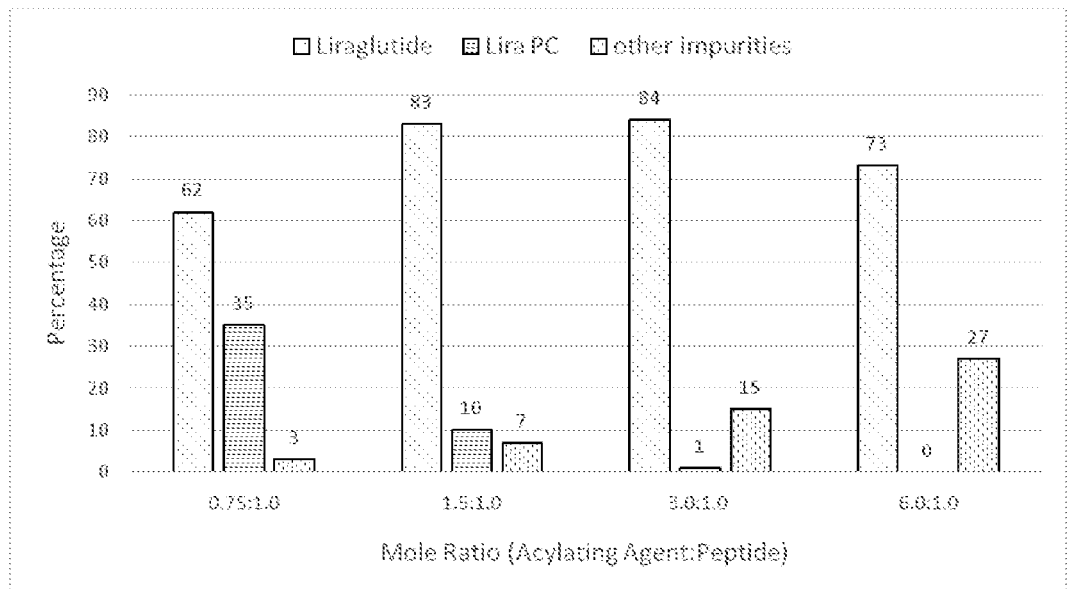
FIG. 7 shows the effect of mole ratio of acylation agent to peptide precursor in the presence of 7.5% TEA in peptide solution on the acylation process. The figure shows the % composition (by area) of the crude reaction mixture comprising of N-substituted precursor (Liraglutide), unreacted liraglutide precursor (Lira PC), and reaction related impurities (other impurities).

100 mg of liraglutide precursor was pre-dissolved in 200 ml aqueous solution containing 7.5% TEA (v/v) and 0.2% TFA (v/v) (approx. concentration 1.5 mM). The pH of the solution was approximately 11.8. Each of the eDAAS containing deprotected N-hexadecanoyl glutamic acid γ-N-hydroxysuccinimide ester having amount: 12.5 mg, 25 mg, 50 mg and 100 mg, was then added to the peptide solution which resulted in approximately 0.75:1, 1.5:1, 3:1 and 6:1 mole ratio of acylation agent to liraglutide precursor respectively. After 10 minutes, pH of the reaction mixture was adjusted to 8.0 using 5 N acetic acid and analyzed using RP-HPLC (FIG. 7).

Yield: As shown in FIG. 7, analytical RP-HPLC analysis showed the conversion to liraglutide ranged from 62% (by area) to 84% (by area). A narrow range of mole ratio of 1.5:1 to 3:1 (acylating agent to peptide) was surprisingly found to yield optimum conversion of liraglutide with near-complete acylation of the liraglutide precursor. The results suggest that although there is a complete conversion of the precursor peptide, the additional amount of acylating agent non-specifically binds to other reactive functional groups including N-terminal amine resulting in higher amount of other impurities.

Example 9: Effect of Acylating Agent Mole Ratio on Conversion Efficacy at 5% TEA in Preparation of N Substituted Peptide 12.5 mg, 25 mg, 50 mg and 100 mg N-hexadecanoyl glutamic acid γ-N-hydroxysuccinimide ester α-tertiary butyl ester (acylation agent) was dissolved in 0.125 ml, 0.250 ml, 0.5 ml and 1 ml of 95% TFA: 5% water, respectively, to obtain a constant concentration of 100 mg/ml. After 1 hour at room temperature and under constant stirring, 1 volume of deprotected N-hexadecanoylglutamic acid γ-N-hydroxysuccinimide ester (DAAS) was equilibrated with one volume of NMP and 2 volumes of TEA to obtain eDAAS (pH 9, 46 mM) at 0-8° C.

Figure 8:
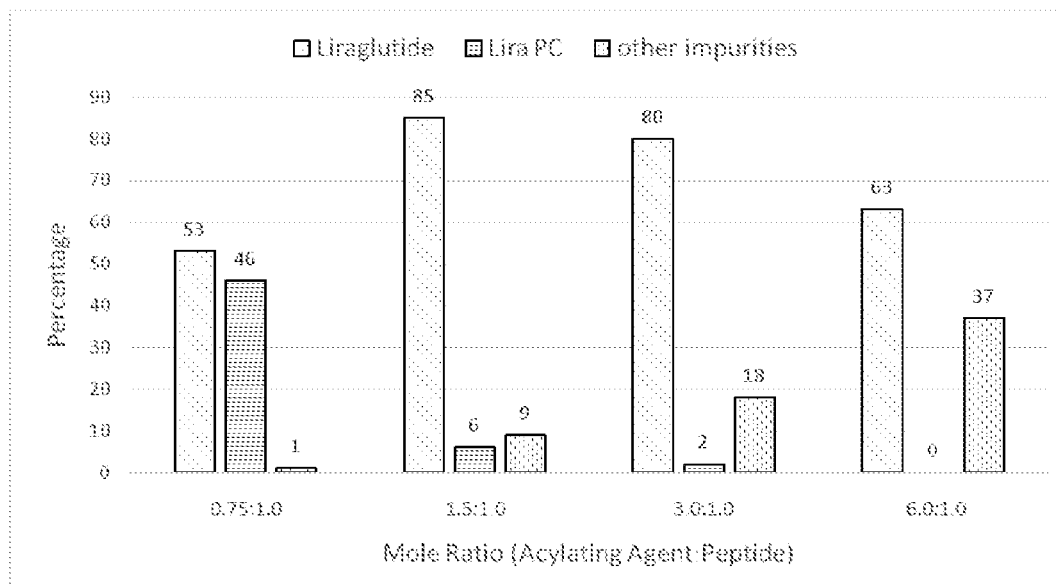
FIG. 8 shows the effect of mole ratio of acylation agent to peptide precursor in the presence of 5% TEA in peptide solution on the acylation process. The figure shows the % composition (by area) of the crude reaction mixture comprising of N-substituted precursor (Liraglutide), unreacted liraglutide precursor (Lira PC), and reaction related impurities (other impurities).

100 mg of liraglutide precursor was pre-dissolved in 200 ml aqueous solution containing 5% TEA (v/v) and 0.2% TFA (v/v) (approx. concentration 1.5 mM). The pH of the solution was approximately 11.5. Each of the eDAAS containing deprotected N-hexadecanoylglutamic acid γ-N-hydroxysuccinimide ester varying amount of 12.5 mg, 25 mg, 50 mg and 100 mg was then added to the peptide solution which resulted in approximately 0.75:1, 1.5:1, 3:1 and 6:1 mole ratio of acylation agent to liraglutide precursor, respectively. After 10 minutes, pH of the reaction mixture was adjusted to 8.0 using 5 N acetic acid and analyzed using RP-HPLC (FIG. 8).

Yield: As shown in FIG. 8, analytical RP-HPLC analysis showed the conversion to liraglutide ranged from 53% (by area) to 85% (by area). The presence of TEA in the equilibration solution was found to also affect the optimum mole ratio of the acylation agent:peptide with 1.5:1 to 3:1 mole ratio giving higher conversion to liraglutide while formation of other impurities were at lower level.

Example 10: Effect of Equilibration Cocktail on Conversion Efficacy at 5% and 10% ACN in Preparation of N Substituted Peptide 250 mg of N-hexadecanoylglutamic acid γ-N-hydroxysuccinimide esterα-tertiary butyl ester (acylation agent) was dissolved in 2.5 ml of 95% TFA: 5% water to obtain a concentration of 100 mg/ml. After 1 hour at room temperature and under constant stirring, 1 volume of deprotected N-hexadecanoylglutamic acid γ-N-hydroxysuccinimide ester (DAAS) was equilibrated with 1volume of NMP and 2 volume of TEA to obtain eDAAS at 0-8° C.

Figure 9:
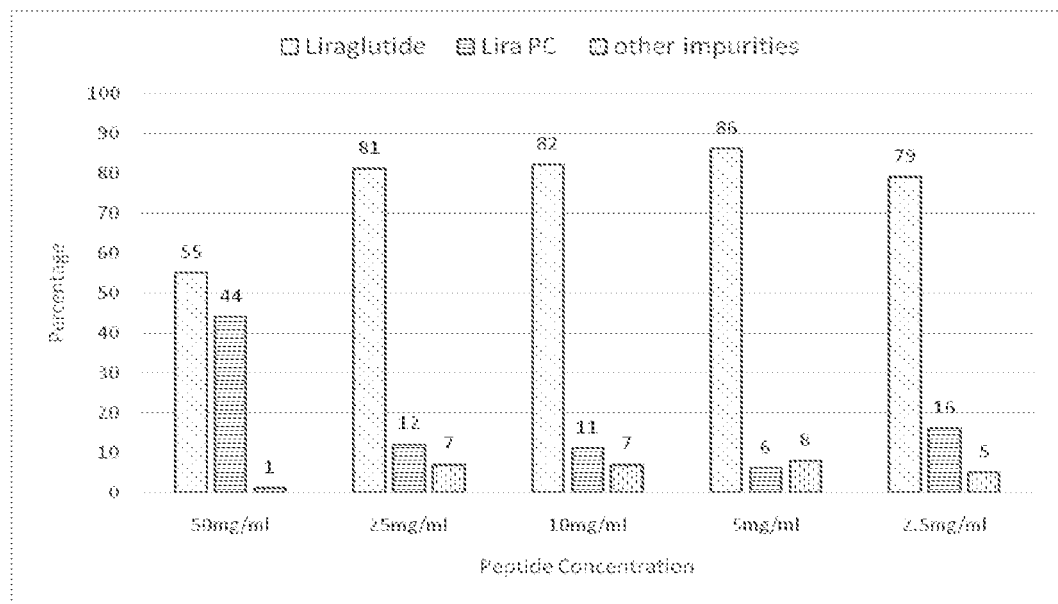
FIG. 9 shows the effect of peptide concentration in peptide solution on the acylation process. The figure shows the % composition (by area) of the crude reaction mixture comprising of N-substituted precursor (Liraglutide), unreacted liraglutide precursor (Lira PC), and reaction related impurities (other impurities).

Various amounts of liraglutide precursor was pre-dissolved in 200 ml aqueous solution containing 7.5% TEA (v/v), 0.2% TFA (v/v) with approx. concentration of peptide as 2.5 mg/ml, 5 mg/ml, 10 mg/ml, 25 mg/ml and 50 mg/ml. The pH of the solution was approximately 11.8. eDAAS containing deprotected N-hexadecanoylglutamic acid γ-N-hydroxysuccinimide ester was then added to each of the peptide solution which resulted in approximately 1.5:1 mole ratio of acylation agent to liraglutide precursor. After 10 minutes, pH of the reaction mixture was adjusted to 8.0 using 5 N acetic acid and analyzed using RP-HPLC (FIG. 9).

Yield: As shown in FIG. 9, analytical RP-HPLC analysis showed the conversion to liraglutide ranged from 55% (by area) to 86% (by area). It was surprisingly found that the peptide concentration in the range of 5-25 mg/ml resulted in higher acylation to liraglutide while peptide concentrations less than 5 mg/ml and higher than 25 mg/ml yielded lower acylation of the liraglutide precursor.

Example 11: Effect of Various Acid Mixtures on Deprotection of Acylating Agent in Preparation of N Substituted Peptide The acylation agent—N-hexadecanoylglutamic acid γ-N-hydroxysuccinimide esterα-tertiary butyl ester was deprotected using various acids namely (i) 95% TFA and 5% Water, (ii) 98% Formic Acid and 2% Water, and (iii) 86% phosphoric acid and 14% Water. All other conditions of the reaction were similar to Example 1 and the peptide to acylating agent mole ratio was 1:3.

Figure 10:
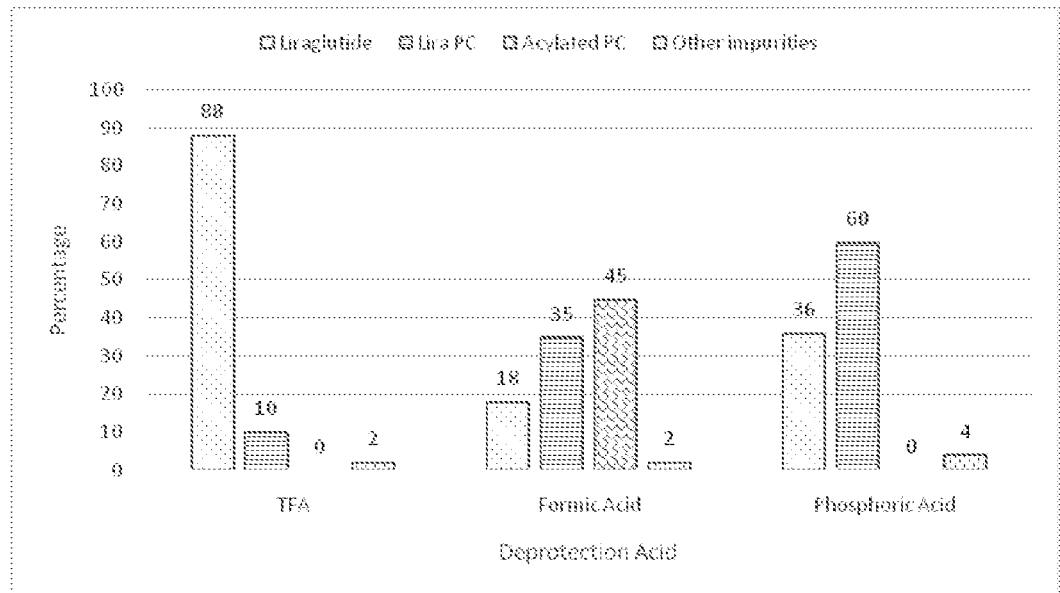
FIG. 10 shows the effect of acylation after deprotection of the acylating agent using various acid mixtures.

Yield: As shown in FIG. 10, analytical RP-HPLC analysis showed the conversion to liraglutide ranged from 18% (by area) to 88% (by area). Deprotection of acylation using TFA yields highest conversion while that of Formic acid generates least conversion. Use of formic acid resulted in incomplete deprotection leading to relatively high amounts of acylated liraglutide with protecting group in the crude mixture. Use of phosphoric acid yielded ~36% conversion, and though absence of acylated liraglutide with protecting group was observed, high amounts of acylating agent was deemed necessary for complete conversion of peptide precursor to liraglutide.

Figure 11:
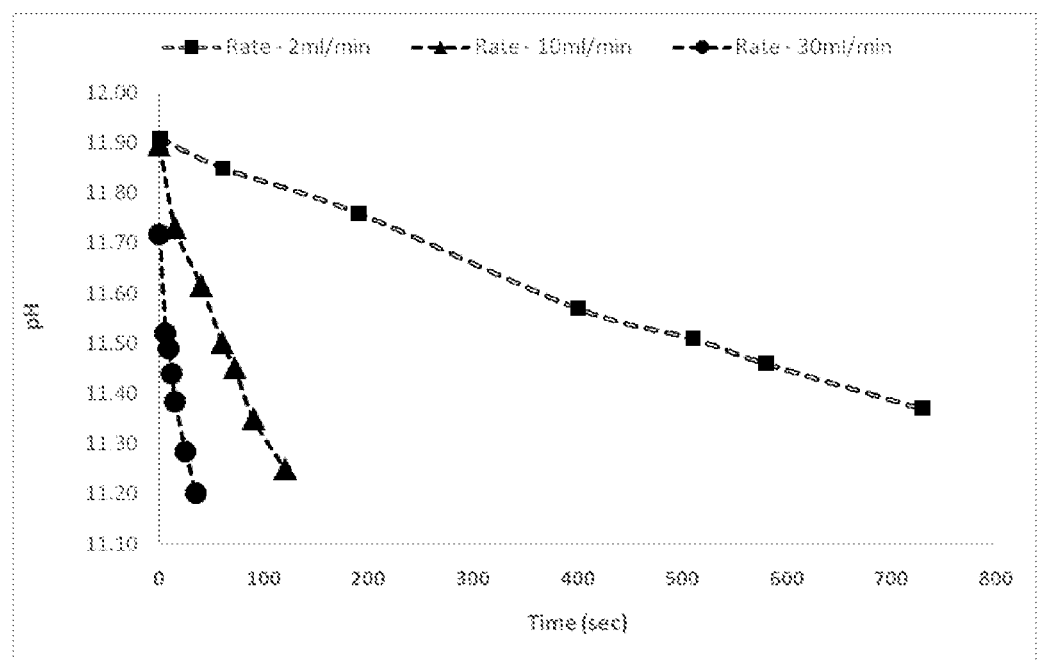
FIG. 11 shows the change in pH of peptide solution in the reaction mixture with change in the rate of addition of eDAAS.

Example 12: Effect of Rate of Addition of eDAAS on pH of Peptide Solution in the Reaction Mixture The condition for acylation of liraglutide precursor peptide was followed as in Example 1, except that the rate of addition of eDAAS solution to the peptide solution was varied from 2 ml/min to 30 ml/min. As seen in FIG. 11, the change in pH was more controlled at rate of addition <10 ml/min. As pH of reaction is critical for optimal conversion to liraglutide, it is important to control the rate of addition of the eDAAS solution to the peptide solution.

From the foregoing, it will be appreciated that, although specific embodiments of the invention have been described herein merely for purposes of illustration, various modifications may be made without deviating from the spirit and scope of the invention and should not be construed so as to limit the scope of the invention or the appended claims in any way.

We claim:

1. A process for acylation of a peptide or a protein comprising an acylatable lysine residue with an acylating agent
comprising a lipophilic moiety, an amino acid group comprising an amine reactive imide ester, and at least one protected carboxyl group comprising an alkyl ester that can be deprotected by hydrolysis under acid conditions;
wherein
said peptide or protein is selected from the group consisting of glucagon-like peptide- 1 (GLP-1), glucagon like peptide-2 (GLP-2), insulin, and analogues thereof, comprising the steps of:
a) deprotection of said acylating agent in a solution comprising a mixture of an acid and a solvent to provide a deprotected acylating agent;
b) equilibrating the deprotected acylating agent of step (a) in a solution at temperature below 25° C. with pH in a basic range;
c) reacting the solution of the equilibrated deprotected acylating agent of step (b) without isolation or purification with a peptide or a protein present in an aqueous solution at basic pH to obtain a N-Substituted peptide or protein; wherein the deprotected equilibrated acylating agent is added to the peptide or protein at a controlled rate to maintain the basic pH; and
d) optionally, quenching the N-Substituted peptide or protein obtained from step (c) by addition of acid or primary amine comprising compound.

2. The process as claimed in claim 1, wherein the lipophilic moiety is is an alkyl lipophilic moiety.

3. The process as claimed in claim 1, wherein the the alkyl ester is tert-butyl ester.

4. The process as claimed in claim 1, wherein the amine reactive imide ester is N-hydroxysuccinimide ester.

5. The process as claimed in claim 1, wherein the concentration of acylating agent in the deprotecting solution of step (a) is in the range of 0.1-1000 mg/ml.

6. The process as claimed in claim 1, wherein the acid in mixture of step (a) is selected from a group comprising trifluoroacetic acid (TEA), phosphoric acid, formic acid, sulfuric acid and hydrochloric acid.

7. The process as claimed in claim 1, wherein the solution for carrying out the deprotection in step (a) comprises 95% TFA and 5% water.

8. The process as claimed in claim 1, wherein equilibration of the deprotected acylating agent in step (b) is achieved by adjusting the pH to a basic pH in a solution comprising a mixture of an aprotic solvent and a base solution.

9. The process as claimed in claim 8, wherein the base solution is selected from a group comprising triethylamine (TEA), alkali metal hydroxide and combinations thereof.

10. The process as claimed in claim 8, wherein the basic pH is in the range of 7 to 12.5.

11. The process as claimed in claim 1, wherein the glucagon-like peptide-1 analogue (GLP-1) is liraglutide precursor.

12. The process as claimed in claim 1, wherein the aqueous solution containing the peptide or the protein in step (c) comprises water, base, acid. aprotic solvent, or combinations thereof.

13. The process as claimed in claim 1, wherein the peptide or protein concentration in the aqueous solution in step (c) is in the range of 1 mg/ml to 30 mg/ml.

14. The process as claimed in claim 1, wherein the basic pH of the peptide or protein in the aqueous solution in step (c) is in the range of 9 to 12.5.

15. The process as claimed in claim 1, wherein the reaction in step (c) between the deprotected equilibrated acylating agent of step (b) with the peptide or the protein is carried out at pH in the range of 10 to 12.

16. The process as claimed in claim 1, wherein the mole ratio of the acylating agent to the peptide or the protein in step (c) ranges from 0.1:1 to 10:1.

17. The process as claimed in claim 1, wherein the quenching of N-Substituted peptide or protein in step (d) is carried out at pH 8.

18. The process as claimed in claim 1, wherein the primary amine comprising compound for quenching N-Substituted peptide or protein is Tris(hydroxymethyl)aminomethane.

19. The process as claimed in claim 1, wherein the protected carboxyl group comprising an alkyl ester is tertiary butyl ester.

20. The process as claimed in claim 1, wherein the amine reactive imide ester is N-hydroxysuccinimide ester.

21. The process as claimed in claim 5, wherein the concentration of acylating agent in the deprotecting solution of step (a) is less than 500 mg/ml.

22. The process as claimed in claim 10, wherein the basic pH is in the range of 9-10.

23. The process as claimed in claim 13, wherein the peptide or protein concentration in the aqueous solution in step (c) is in the range of 5 mg/ml to 25 mg/ml.

24. The process as claimed in claim 14, wherein the basic pH of the peptide or protein in the aqueous solution in step (c) is in the range of 11.2 to 11.8.

25. The process as claimed in claim 15, wherein the pH in the reaction in step (c) between the deprotected equilibrated acylating agent of step (b) with the peptide or the protein is carried out at pH in the range of 10.5 to 11.8.

26. The process as claimed in claim 16, wherein the mole ratio of the acylating agent to the peptide or the protein is in the range of 1.5:1 to 3:1.

27. A process for acylation of a acylatable peptide or protein comprising a liraglutide precursor having amino acid sequence as set forth in SEQ ID NO. 1, with a protected acylating agent having amino acid group comprising a tertiary butyl ester carboxyl protecting group, a N-hydroxysuccinimide ester reactive ester group and a N-hexadecanoylglutamic acid lipophilic moiety, said acylating agent having the following structure:

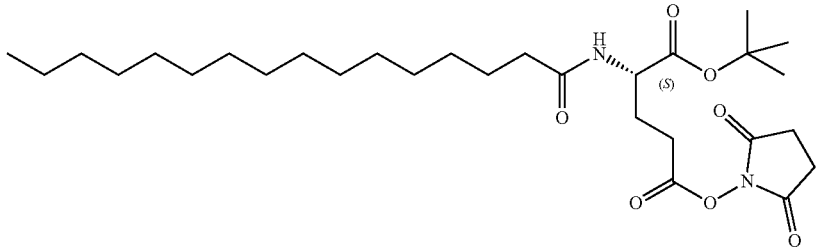

comprising the steps of:
a) deprotection of said protected acylating agent in a solution comprising a mixture of an acid comprising trifluoroacetic acid (TFA) and an aqueous solvent to provide a deprotected acylating agent;
b) equilibrating the deprotected acylating agent of step n a solution at temperature below 25° C. with pH in a basic range;
c) reacting the solution of the equilibrated deprotected acylating agent of step (b) without isolation or purification with a peptide or a protein present in an aqueous solution at basic pH to obtain N-substituted peptide or protein; wherein the deprotected equilibrated acylating agent is added to the peptide or protein at a controlled rate to maintain the basic pH; and
d) optionally, quenching the N-Substituted peptide or protein obtained from step (c) by addition of trifluoroacetic acid (TFA) or tris(hydroxymethyl)aminomethane.

28. The acylating agent in claim 1 wherein the lipophilic moiety is a hexadecanoyl glutamic acid, the amine reactive ester is N-hydroxysuccinimide ester and the protected carboxyl group comprising an alkyl ester is tent-butyl ester.

* * * * *